US010561804B1

(12) United States Patent
Culligan

(10) Patent No.: US 10,561,804 B1
(45) Date of Patent: Feb. 18, 2020

(54) WIRELESS SYSTEM AND DEVICE FOR PHYSICAL STATE CONVERSION AND DELIVERY OF A TARGET MEDICINAL SUBSTANCE TO A USER

(71) Applicant: Chris Culligan, Golden, CO (US)

(72) Inventor: Chris Culligan, Golden, CO (US)

( * ) Notice: Subject to any disclaimer, the term of this patent is extended or adjusted under 35 U.S.C. 154(b) by 227 days.

(21) Appl. No.: 15/444,292

(22) Filed: Feb. 27, 2017

Related U.S. Application Data

(60) Provisional application No. 62/300,145, filed on Feb. 26, 2016.

(51) Int. Cl.
*A61M 11/04* (2006.01)
*A61M 15/00* (2006.01)
*H05B 1/02* (2006.01)

(52) U.S. Cl.
CPC ...... *A61M 11/042* (2014.02); *A61M 15/0086* (2013.01); *H05B 1/0244* (2013.01); *A61M 2205/3368* (2013.01); *H05B 2203/021* (2013.01)

(58) Field of Classification Search
CPC ............ A61M 11/042; A61M 15/0086; A61M 2205/3368; H05B 1/0244; H05B 2203/021
USPC .............................. 128/203.27, 200; 131/173
See application file for complete search history.

(56) References Cited

U.S. PATENT DOCUMENTS

| | | | |
|---|---|---|---|
| 7,565,908 B2 * | 7/2009 | Liu | A24F 1/30 131/173 |
| 2016/0015083 A1 * | 1/2016 | Castillo | A24F 47/008 131/329 |

* cited by examiner

*Primary Examiner* — Imani N Hayman
(74) *Attorney, Agent, or Firm* — Smith Tempel Blaha LLC; Matthew T. Hoots

(57) ABSTRACT

A device for incineration and/or vaporization of a target medicinal substance and a method of using the same are disclosed.

6 Claims, 5 Drawing Sheets

WIRELESS SYSTEM AND DEVICE FOR PHYSICAL STATE CONVERSION AND DELIVERY OF A TARGET MEDICINAL SUBSTANCE TO A USER

BACKGROUND

The present invention relates to drug delivery systems and, more particularly, to a system and device operable to vaporize a target liquid or combust a target substance in a chamber that is configured for wireless connection to a power source. As any user of nebulizer or smoke generating systems known in the art will attest, a constant annoyance is dealing with electrical wires that limit the portability and convenience of using the system.

Therefore, what is needed in the art is a wireless system and device that converts the physical state of a target medicinal substance and provides a user with the ability to inhale a resulting vapor or smoke from a chamber that wirelessly connects to a power source.

BRIEF SUMMARY OF THE INVENTION

Various embodiments, aspects and features of the present invention comprise an expansion chamber with a heating coil, an electrical controller and a docking station. The docking station may be electrically connected to the controller that, in turn, is electrically supplied from a power source. The expansion chamber is configured to receive a target medicinal substance for vaporizing or incinerating, as dictated by the physical nature of the substance, by an integrated heating coil. When the expansion chamber is in mechanical and electrical connection with the docking station (i.e., it is "docked"), the heating coil is provided power according to the configuration of the controller to control the thermal energy generated by the heating coil. As such, when docked, the thermal energy generated by the heating coil may work to vaporize or incinerate a target substance so that an inhalable vapor or smoke is generated and contained within the expansion chamber. Subsequently, the user may "pick up" the expansion chamber, thereby decoupling it from the docking station, for easy and convenient inhalation of the vapor or smoke.

DRAWINGS

DESCRIPTION

The Figures and the related description are offered for illustrative purposes and collectively depict exemplary embodiments of a wireless system and device for physical state conversion and delivery of a target medicinal substance to a user. As such, the exemplary embodiments shown in the Figures do not illustrate all features and aspects that may be included in a given embodiment of the solution. For instance, it is envisioned that an embodiment of the solution may include printed circuit boards configured to electrically connect when the system is in a docked state. Moreover, it is envisioned that an embodiment of the solution may comprise any number of vapor or smoke chambers for aggregating and dispensing generated vapor or smoke to a user. Further, it is envisioned that embodiments of the solution, or components thereof, may vary in size and/or configuration depending on the particular intended use of the system. Even further, it is envisioned that embodiments of the solution may comprise an integrated, chargeable power source (such as a battery) configured to provide power to a heater element and receive a replenishing charge when the system is in a docked state.

With reference to FIG. 1-FIG. 4, base station 1010 includes an upper surface 1120 and one or more vertical support walls 1130. A power switch 1150 and/or temperature indicator 1140 may be integrated with one more walls 1130. Base station 1010 includes an electrical power connection and an interface and/or power converter for operational connection to controller 1020.

Figure 1:
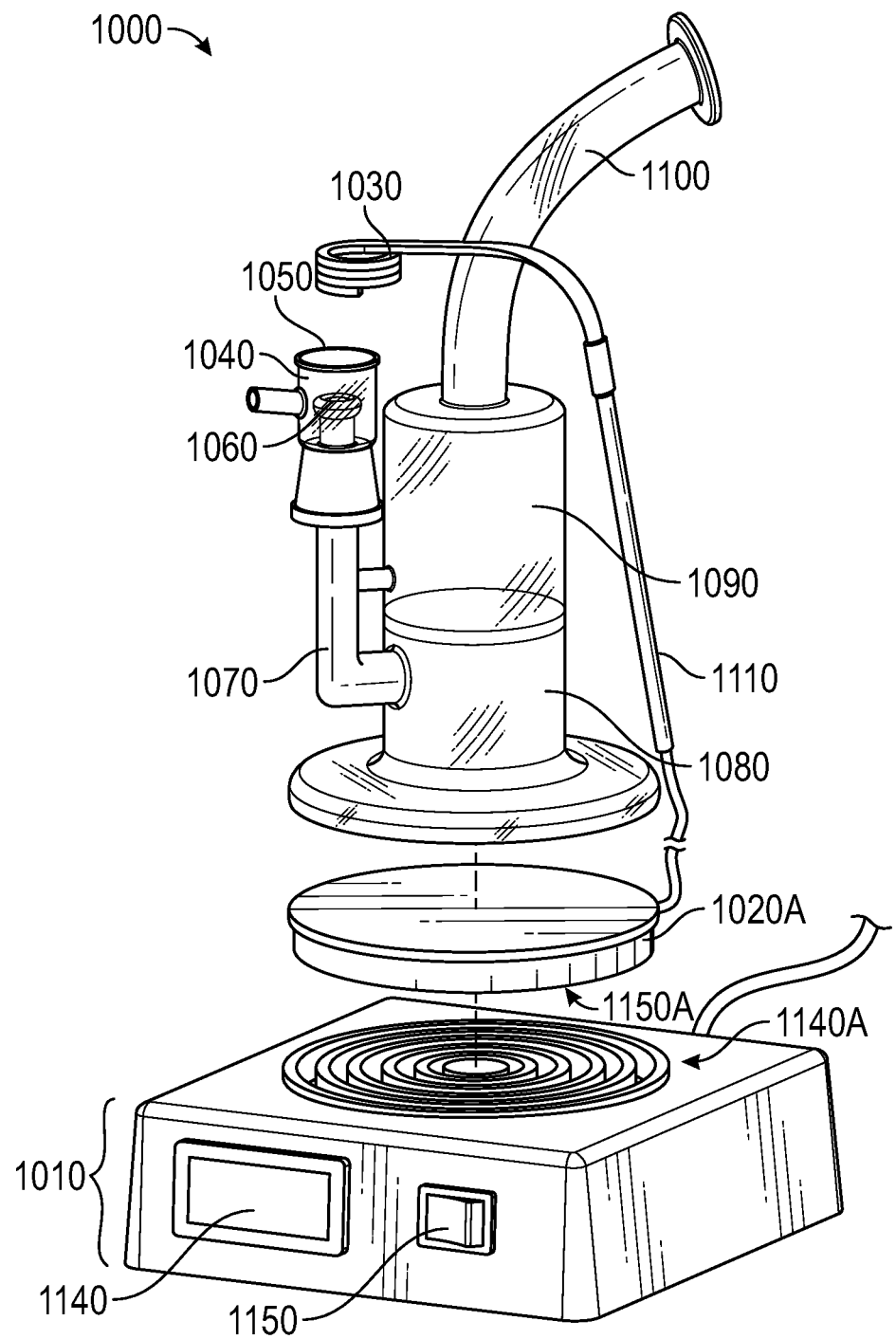
FIG. 1 shows a perspective exploded view of a first embodiment of a device including a heating coil, an electrical controller and a docking station.
Figure 3:
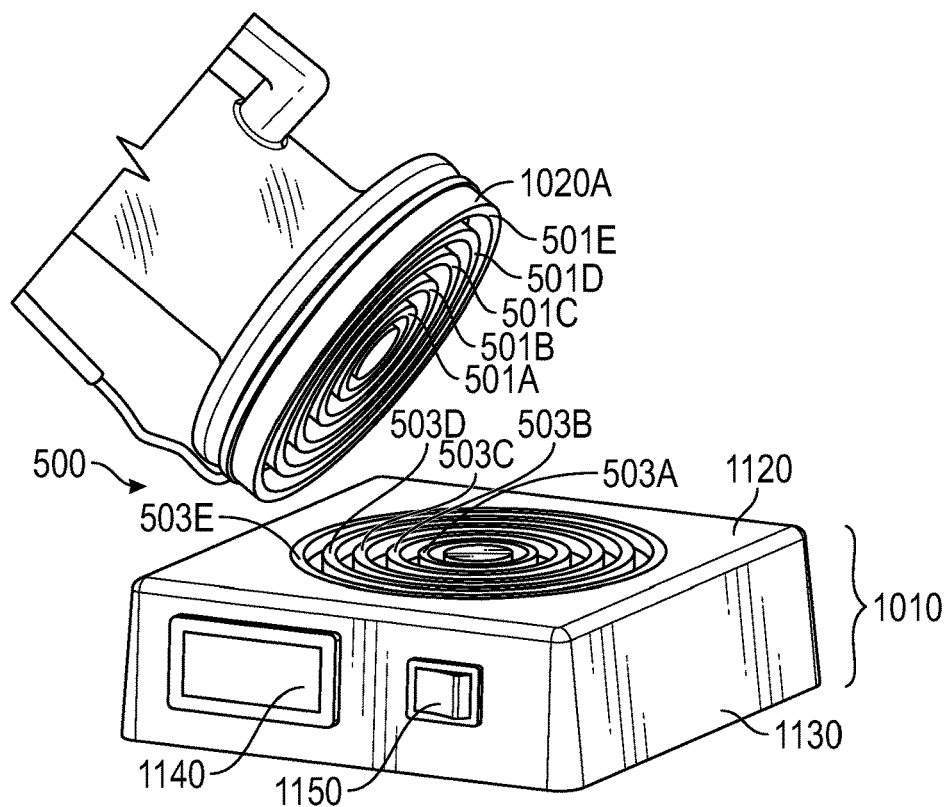
FIG. 3 shows a perspective view of the interface between the docking station and the electrical controller of the first embodiment of FIG. 1.

With reference to FIG. 1 and FIG. 3, a first embodiment of a device 1000 includes a base station 1010, controller 1020A in electronic communication with base station 1010, and coil 1030 in electronic communication with controller 1020A. Coil 1030 is shaped to encircle, or wrap around, the exterior wall of crucible 1040. The interior 1050 of crucible 1040 is shaped to hold a substance, liquid or solid, to be incinerated to a smoke, or vaporized to a gas, respectively, as known to those of skill in the art. Such a vapor or smoke is pulled through opening 1060 into tube 1070, then through liquid (e.g., water) 1080 held in expansion chamber 1090. Finally, smoke and/or vapor is pulled by suction through tube 1100 which is in fluid communication with a user or other device.

Controller 1020A is in electronic communication with base station 1010 by an interface comprising a lower interface portion 1140A and an upper interface portion 1150A. With reference to FIG. 1 and FIG. 3, upper interface portion 1150A may comprise a series of concentric electrical contact surfaces 501A-E that are raised above a base surface of controller 1020. Lower interface portion 1140A, abutting an upper portion of base station 1010, may comprise a series of concentric electrical contact surfaces 503A-E. When upper and lower interface portions 1140A and 1150A meet, said portions may be in electronic communication. In this way, surfaces 501A and 503A; and/or 501B and 503B; and/or 501C and 503C; and/or 501D and 503D; and/or 501E and 503E are substantially meeting, e.g. flush one against the other. The electrical contact surfaces 501 and/or 503 may be electrically connected to the various I/O associated with the heater coil 1030 through a cord 1110. Cord 1110 may include electrical connections such as neutral, ground, thermocouple and/or positive/negative. The controller 1020 may be configured to mount on a surface of an expansion chamber 1090 such that cord 1110 connecting 1020 the heater coil 1030 extends proximate to and/or along an outside surface of expansion chamber 1090.

Figure 2:
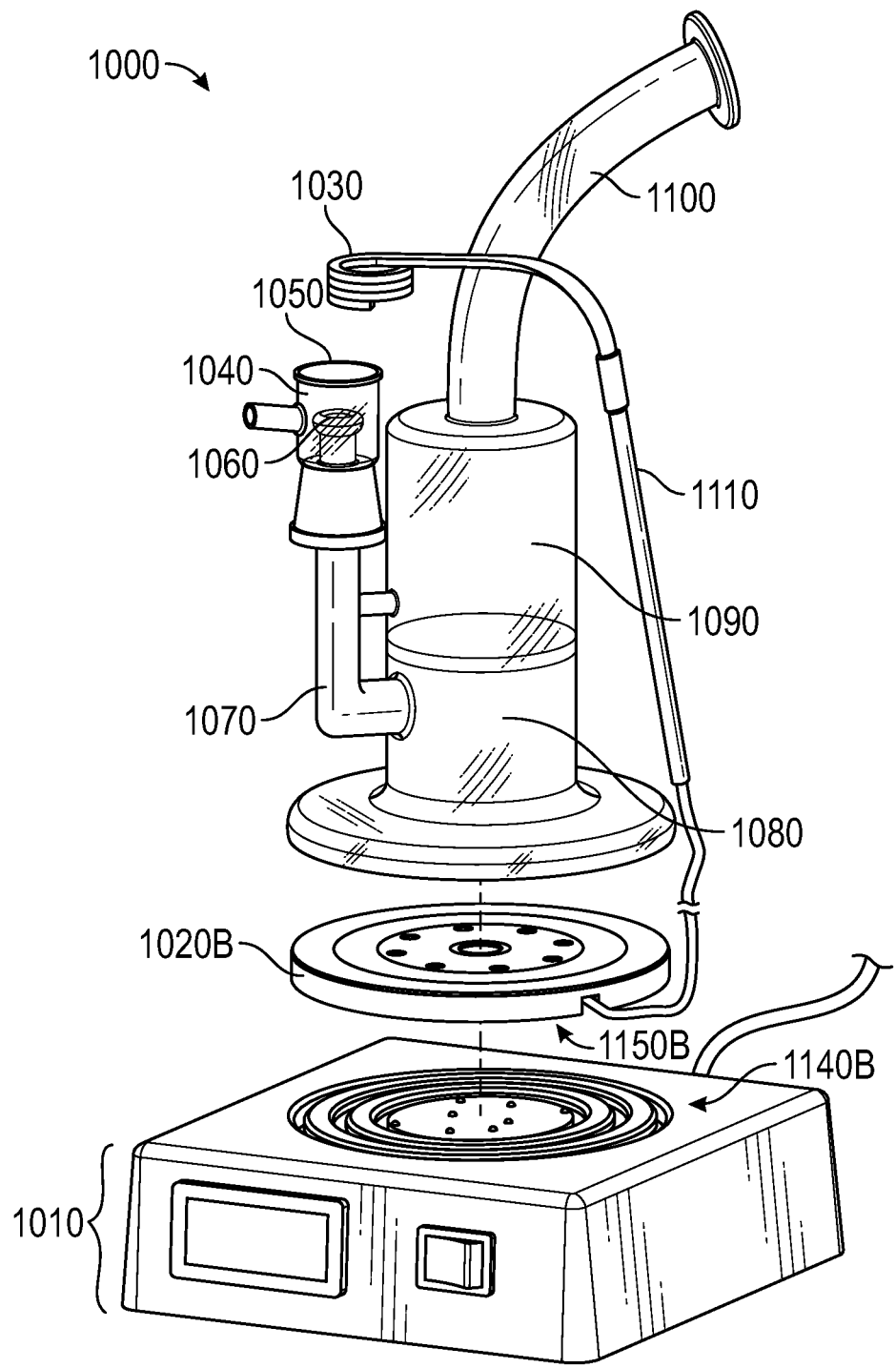
FIG. 2 shows a perspective exploded view of a second embodiment of a device including a heating coil, an electrical controller and a docking station.
Figure 4:
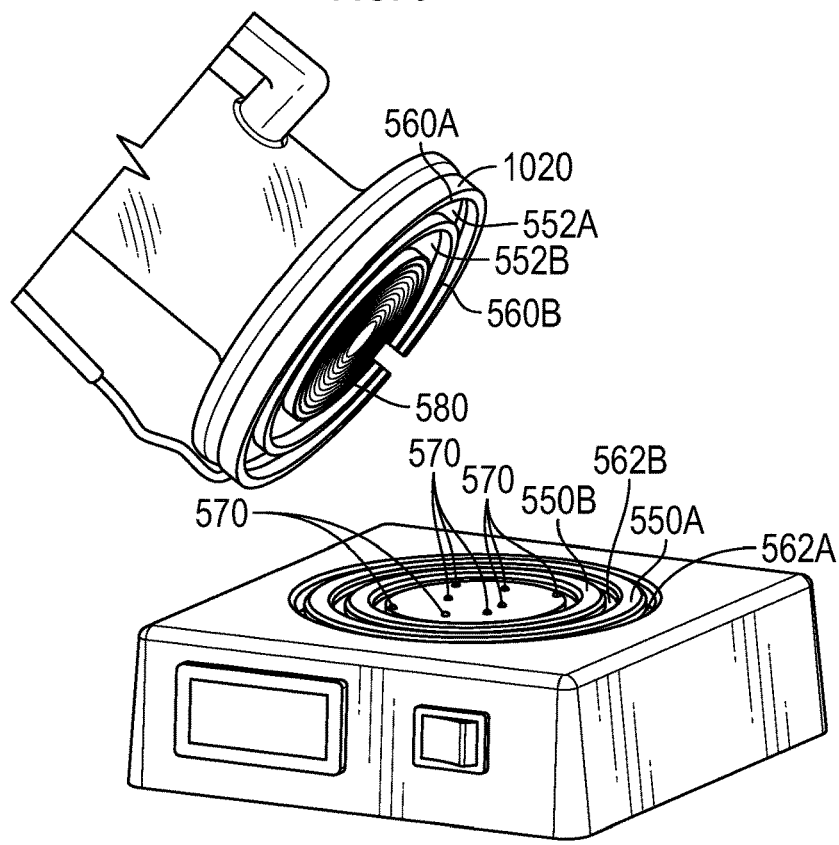
FIG. 4 shows a perspective view of the interface between the docking station and the electrical controller of the second embodiment of FIG. 2.

With reference to FIG. 2 and FIG. 4, in an alternative embodiment, an interface between controller 1020B and base 1010 may comprise raised ridges 550A and 550B which may engage concentric grooves 552A and 552 B, respectively. Concomitantly, raised ridges 560A and 560B may engage groves 562A and 562B, respectively. In this way, one or more contact points 570 may be in electrical communication with configured connection points on the lower surface of controller 1020B, e.g., a set of concentric ridges 580. The electrical contact surfaces 570 and 580 may be electrically connected to the various I/O associated with the heater coil 1030 through a cord 1110. Cord 1110 may include electrical connections such as neutral, ground, thermocouple and/or positive/negative. The controller 1020B may be configured to mount on a surface of an expansion chamber 1090 such that cord 1110 connecting 1020 the heater coil 1030 extends proximate to and/or along an outside surface of expansion chamber 1090.

Figure 5:
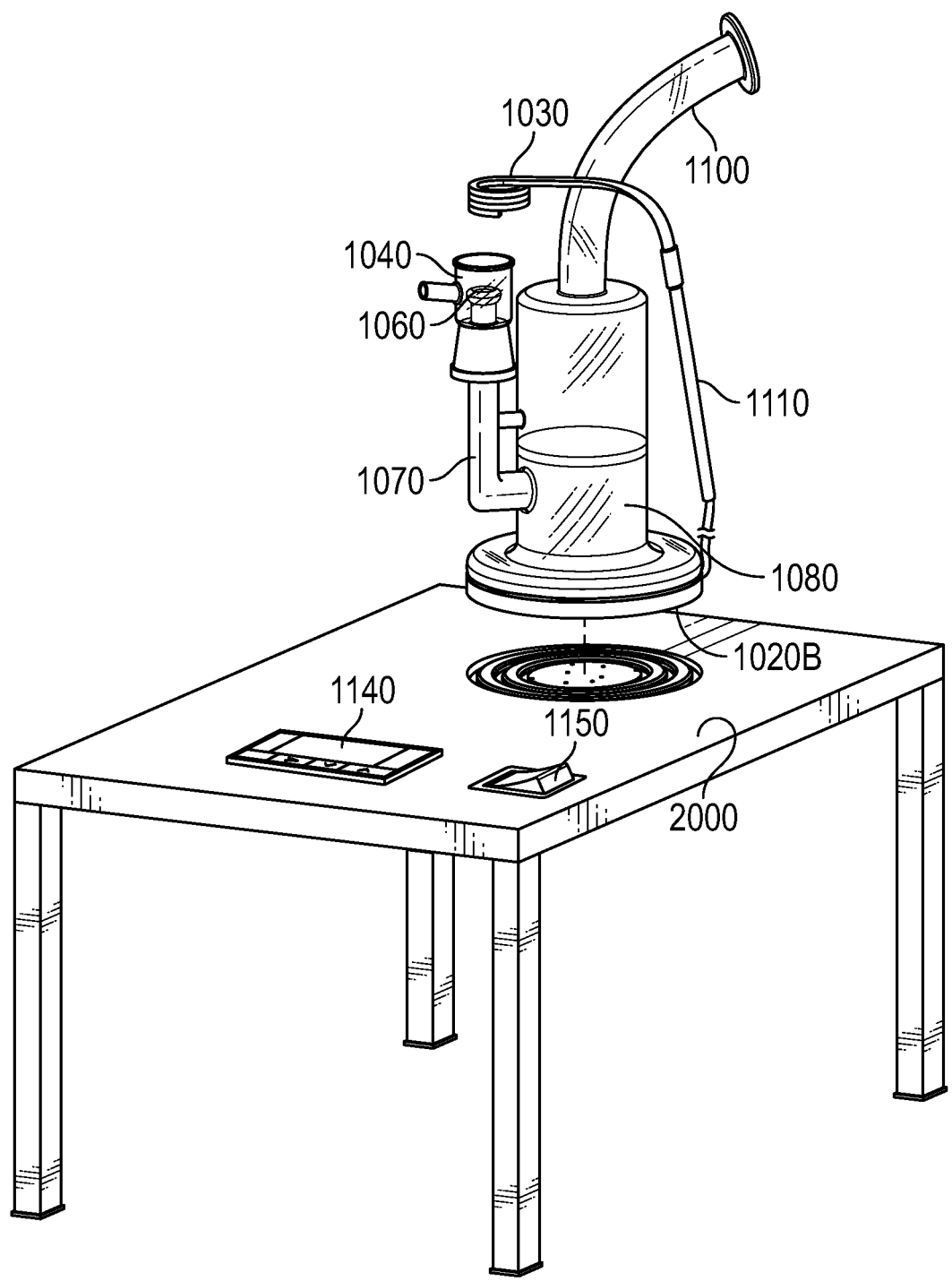
FIG. 5 shows a perspective view of the device of FIG. 1 wherein the docking station is integrated with a surface, e.g., a flat surface of a table or platform; and wherein electrical controller switches are separated from the docking station, e.g., integrated with the platform.

With reference to FIG. 5, in an alternative embodiment, the base station may be integrated with or into another surface. For example, lower portion 1140A may be mounted on or in a surface 2000. Temperature and power switches 1140 and 1150 may be mounted on the surface; or alternatively, temperature and power may be wirelessly controlled through a wireless connection module integrated with lower portion 1140A. In another alternative embodiment, a wireless connection module may be integrated into base station 1010.

Figure 6:
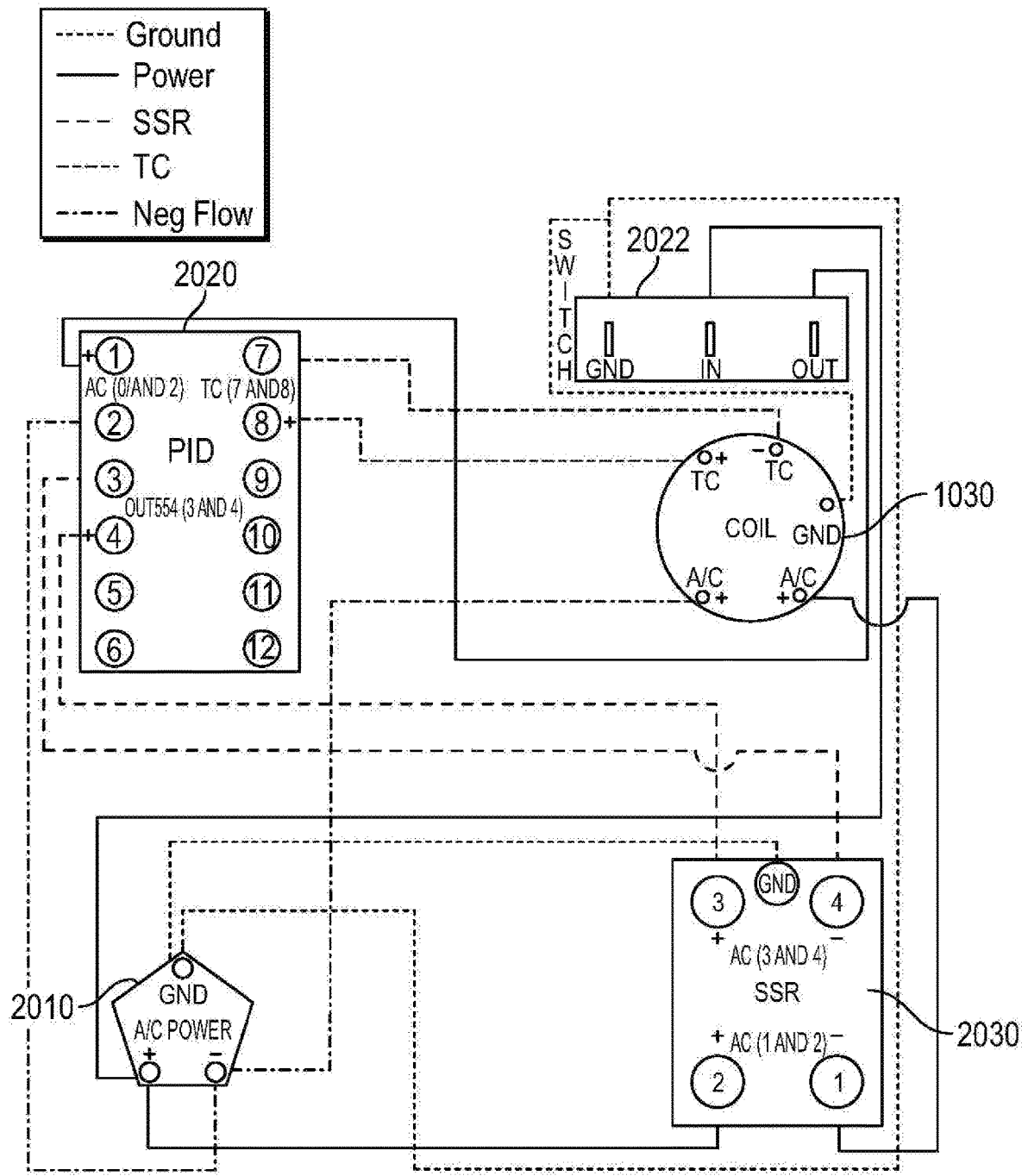
FIG. 6 is a general electrical schematic of various components that may be comprised within an exemplary electrical controller.

As can be seen in the FIG. 6. exemplary illustration, a proportional integral derivative ("PID") controller 2020 is in electrical communication with a power source 2010, a switch 2022, a solid state relay ("SSR") 2030, a multi-pin connector interface, and a heater coil 1030. The heater coil includes thermocouples "TC" (or any suitable temperature sensor) configured to provide temperature feedback to the PID controller. As would be understood by one of ordinary skill in the art, the PID controller leverages the temperature feedback to adjust a power supply to the coil, thereby affecting and controlling the amount of thermal energy generated by the coil. In this way, precise control of the temperature associated with the coil output may be maintained.

The term controller may include one or more modules and or interfaces as known to the person of ordinary skill in the art. Such modules and interfaces may be adapted as known to the person of ordinary skill.

Notably, although the exemplary embodiments shown and described herein include a cord 1110 between the heating coil 1030 and the controller 1020 that extends along the outside of an expansion chamber 1090, embodiments of the solution are not limited to such a configuration. For example, it is envisioned that a "cord" comprising electrical connections between a heater coil and a docking plate interface may be integral to the expansion chamber in some embodiments. In such embodiments, the expansion chamber may include an electrical connection point for the heater coil to the integral cord, and another for the docking plate interface, such that the heater coil and/or docking plate interface may be easily removed for maintenance or replaced.

Additionally, although the exemplary embodiments e.g., the controller, docking plate interfaces shown and described herein, comprise a series of raised, concentric electrical connections, embodiments of the solution are not limited to such an arrangement for a docking plate interface. For example, it is envisioned that a printed and etched circuit board may be used as a docking plate interface. Further, it is envisioned that a series of parallel electrical connections, or any suitable geometric arrangement for that matter, may be comprised within an embodiment of the proposed solution. Moreover, embodiments of the solution are not limited to any particular number of electrical connections and/or positioning features. For example, one or more pins and/or indentions on a docking plate interface may be used as a positioning feature. In another embodiment, controller 1020 may comprise a battery sufficient to heat coil 1030. Such a battery may be charged by inductive coupling with an inductor in base 1010. The battery may be charged by electrical connection through the interface, e.g., 1040A and 1050A; and/or 1040B and 1050B.

In another embodiment, a method for delivering a target liquid or substance to a person in need thereof may comprise placing device 1000 in a ready position wherein base station 1010, controller 1020, coil 1030, and expansion chamber 1090 are in physical and electrical communication, loading the target liquid substance into crucible 1040, selecting a temperature to which to head the target liquid or substance, heating coil 1030 to the selected temperature, and removing expansion chamber 1090 and controller 1020 off the base. A user, or a device, may apply a vacuum to tube 1100 thus drawing air through crucible 1040 to release smoke and or vapor throughout the tubes 1070, 1090, and 1100 and to the user or device applying a vacuum. When the crucible 1040 has cooled, the expansion chamber 1090 may be replaced on base station 1010 and the process repeated.

Various aspects, features and characteristics of the present invention have been described. Not all of the aspects, features or characteristics are required for each and every embodiment of the present invention. However, it will be appreciated that the various aspects, features, characteristics and combinations thereof may be considered novel in and of themselves.

What is claimed is:

1. A device for incineration and/or vaporization of a target medicinal substance comprising:
   a base comprising an electrical power source for electrically energizing the base;
   a controller detachably mounted to the base and operable to receive electrical power from the base when in mechanical contact with the base, wherein, when the detachably mounted controller is detached from the base, the base remains electrically energized;
   a crucible mounted on the controller; and
   a heating coil in electronic communication with the controller and in mechanical contact with the crucible such that when the controller receives electrical power from the base the controller supplies electrical energy to the heating coil such that the heating coil generates thermal energy that operates to raise a temperature in the crucible to a selected temperature;
   wherein the controller comprises one or more raised ridges and the base comprises one or more grooves such that when the controller is in mechanical contact with the base the one or more raised ridges are received into the one or more grooves in order to generate mechanical and electrical communication between the controller and base.

2. The device of claim 1 wherein the controller reduces the electrical energy supplied to the heating coil when the selected temperature is achieved.

3. The device of claim 1 wherein the crucible is in fluid communication with a user of the incinerated and/or vaporized target medicinal substance.

4. The device of claim 3 wherein the crucible is in fluid communication with an expansion chamber.

5. The device of claim 1, wherein the one or more raised ridges comprised within the controller are comprised of a first series of concentric electrical contact surfaces and the one or more grooves comprised within the base are comprised of a second series of concentric electrical contact surfaces.

6. A method of delivering a target medicinal substance to a subject in need thereof comprising loading the substance into the crucible of claim 1, heating the crucible to a selected temperature, optionally removing the controller from the base, and providing a vapor and/or smoke from the heated crucible to the subject.

* * * * *